United States Patent [19]

Arai et al.

[11] Patent Number: 4,535,190
[45] Date of Patent: Aug. 13, 1985

[54] PHENOLIC COMPOUNDS AND A HEAT-SENSITIVE RECORDING MATERIAL CONTAINING THE SAME

[75] Inventors: Naoto Arai; Takeshi Murakami; Toshitake Suzuki, all of Hyogo; Toranosuke Saito, Osaka; Masakatu Kitani, Hyogo; Takashi Ishibashi, Osaka, all of Japan

[73] Assignees: Sanko Kaihatsu Kagaku Kenkyusho, Osaka; Kanzai Paper Manufacturing Company Ltd., Tokyo both of Japan

[21] Appl. No.: 592,598

[22] Filed: Mar. 23, 1984

[30] Foreign Application Priority Data

Mar. 25, 1983 [JP] Japan .................. 58-48939

[51] Int. Cl.³ .................. C07C 39/17; C07C 39/12
[52] U.S. Cl. .................. 568/721; 568/718; 568/722
[58] Field of Search .................. 568/721, 722, 718, 717

[56] References Cited

U.S. PATENT DOCUMENTS

| | | | |
|---|---|---|---|
| 2,883,365 | 4/1959 | Mathes .................. | 568/721 |
| 2,894,004 | 7/1959 | Dietzler .................. | 568/721 |
| 3,408,407 | 10/1968 | Cotter et al. .................. | 568/721 |
| 3,539,375 | 11/1970 | Baum .................. | 428/331 |
| 4,283,458 | 8/1981 | Igerashi et al. .................. | 428/341 |

FOREIGN PATENT DOCUMENTS

| | | | |
|---|---|---|---|
| 4514039 | 12/1964 | Japan .................. | 568/721 |
| 48-27736 | 12/1973 | Japan .................. | 568/721 |

*Primary Examiner*—Werren B. Lone
*Attorney, Agent, or Firm*—Kane, Dalsimer, Kane, Sullivan and Kurucz

[57] ABSTRACT

Novel phenolic compounds useful as a color developer suitable for satisfying the quality requirements of heat-sensitive recording materials are provided, which compounds are expressed by the general formula

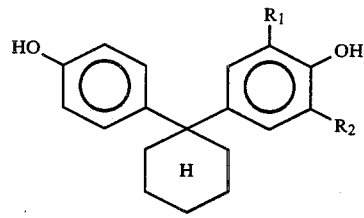

wherein $R_1$ represents an alkyl group or a cycloalkyl group and $R_2$ represents hydrogen atom or an alkyl group; and also heat-sensitive recording materials usable in a broad application field are provided, which recording materials are provided with a heat-sensitive recording layer composed mainly of a colorless basic dye and the above compounds as a color developer by which the dye forms colors, overlaid on a substrate.

2 Claims, No Drawings

PHENOLIC COMPOUNDS AND A HEAT-SENSITIVE RECORDING MATERIAL CONTAINING THE SAME

BACKGROUND OF THE INVENTION

This invention relates to phenolic compounds and a heat-sensitive recording material containing the same as a color developer.

As already known from Japanese Patent Publication No. Sho 43-4160/1968, No. Sho 45-14039/1970, Japanese Patent Application Laid-Open No. Sho 48-27736/1973, etc., heat-sensitive recording materials (hereinafter abbreviated merely to recording materials) consist of a heat-sensitive recording layer composed mainly of a colorless or light-colored basic color-forming substance (dye) and an acidic color developing substance (color developer) and a substrate supporting the layer, and when the dye and the color developer are subjected to fusion by heating, a recorded image is obtained by forming a deep, developed color phase. Such heat-sensitive recording materials have been broadly applied mainly to instrumentation recording, terminal recording of information and communication apparatus, output recording of computer, etc.

However, the advance of heat-sensitive recording apparatus and the extension of the application field of the recording materials have been becoming notable, and along with this, a higher level of the qualities of the recording materials have been required. As particularly desired qualities, the whiteness of the recording materials, the stability of records, and the heat response properties of the recording materials may be exemplified.

The whiteness of the recording materials is a specific feature which makes clearer the resulting recorded images which in turn resort directly to vision; hence the whiteness should be said to be an important quality of the materials. To reduce the whiteness of the recording materials has been usually called "fogging" and it is often observed when the color developer used has a particularly low melting point or is somewhat water-soluble. During the production process of the recording materials or during their storage, a color development already somewhat occurs over the surface thereof. Particularly in the case of bisphenol A having often been used as a color developer, it has been known that fogging is caused by its water-solubility. In order to prevent this fogging, a method of adding a slightly desensitizable substance has occasionally been employed, but the method is said to be undesirable since it reduces the intrinsic color-forming properties of the recording materials.

The stability of records represents how long the records do not lose their images in an environment wherein the records are usually preserved. As to the cause for which the records are damaged, many ones have already been known such as (1) reduction in the concentration of developed color phase due to vaporization of color developers, (2) reduction in the concentration of developed color phase due to photochemical deterioration, (3) desensitizing function of developed color due to environmental substances, (4) extinction of developed color phase due to phase separation of developed color phase or bleeding of color developer from developed color phase, etc.

The heat response properties represent in what short time or with what minute energy for heating the development of the recorded images is carried out. This specific feature has usually been supplemented by adding a third substance (sensitizer).

Generally bisphenol A (2,2-di(4-hydroxyphenyl)-propane) has often been used as a color developer. Bisphenol A has a deep color-developing function, but it is practically considerably unsatisfactory in respect of the whiteness of the recording materials, the stability of records or the heat response properties of the recording materials.

On the other hand, 1,1-di(4-hydroxyphenyl)-cyclohexane has been known to provide a recording material which is inferior in the heat response properties of recording materials but particularly superior in the stability of records. This is presumed to be caused by either a fact that 1,1-di(4-hydroxyphenyl)cyclohexane forms a developed color phase having an extremely high viscosity with dyes, or a fact that the compound has a specifically strong interaction with dyes.

The causes for which the stability of records is damaged are as described above; however, particularly when it is required to preserve the records for a long time, the phase separation of the color developed phase may be a most important problem. The developed color phase consists of a thermodynamically unstable non-crystalline phase, and there is a tendency that at least one of the color developer and the dye contained therein causes much or less phase separation from the non-crystalline phase in the form of an independent crystalline phase, respectively. When the color developed phase is extinct, the color-developed concentration becomes nil; hence the records are lost. The extinction of the color-developed phase due to the phase separation is easily confirmed since the phase is temporarily regenerated by reheating. In general, the resistance to the tendency of the phase separation consists in the viscosity of the color-developed phase. The higher the viscosity of the color-developed phase, i.e. the higher the glass transition point of the color-developed phase, the slower the tendency of the phase separation.

SUMMARY OF THE INVENTION

The object of the present invention is to provide novel phenolic compounds as a color developer suitable for satisfying the quality requirements of heat-sensitive recording materials, and recording materials using the same, usable within a broad application field.

The present invention resides in as a first aspect, novel phenolic compounds expressed by the general formula I

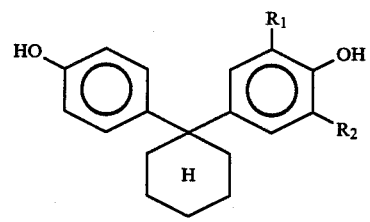

wherein $R_1$ represents an alkyl group or a cycloalkyl group and $R_2$ represents hydrogen atom or an alkyl group, and as a second aspect, a heat-sensitive recording material containing at least one kind of the same.

DETAILED DESCRIPTION OF THE INVENTION

The compounds of the present invention expressed by the general formula I form a color-developed phase having an extremely high viscosity, which is all the same as that of the above 1,1-di(4-hydroxyphenyl)cyclohexane to thereby retain a superior stability of records, and yet since the compounds have low melting points due to their unsymmetrical structures and also a superior compatibility with sensitizers, it is possible to provide a recording material having superior heat response properties. Further since the compounds are far more water-insoluble than bisphenol A, it goes without saying that the compounds provide a recording material having a superior whiteness.

Thus the compounds of the general formula I are furnished with specific features due to which it is possible to provide a recording material which is at the same time superior in the whiteness of recording materials, the stability of records and the heat response properties of recording materials, which specific features have never been observed with so far known bisphenol compounds.

In the general formula I, $R_1$ represents an alkyl group or cycloalkyl group the carbon number thereof being preferably in the range of 1 to 6, and $R_2$ represents hydrogen atom or an alkyl group, its carbon number being preferably in the range of 1 to 6. Examples of the alkyl group or cycloalkyl group which is desirable for the object of the present invention are methyl, ethyl, isopropyl, tertiary-butyl and cyclohexyl. Further, concrete examples of the compounds of the formula I are 1-(4-hydroxyphenyl)-1-(3-methyl-4-hydroxyphenyl)cyclohexane, 1-(4-hydroxyphenyl)-1-(3,5-dimethyl-4-hydroxyphenyl)cyclohexane, 1-(4-hydroxyphenyl)-1-(3-ethyl-4-hydroxyphenyl)cyclohexane, 1-(4-hydroxyphenyl)-1-(3-isopropyl-4-hydroxyphenyl)cyclohexane, 1-(4-hydroxyphenyl)-1-(3-tertiary-butyl-4-hydroxyphenyl)cyclohexane and 1-(4-hydroxyphenyl)-1-(3-cyclohexyl-4-hydroxyphenyl)-cyclohexane. All of these unsymmetrical bisphenol compounds can be prepared with good efficiency by reacting o-substituted phenols with p-cyclohexenylphenol in the presence of an acidic catalyst. The chemical process is expressed by the following chemical equation:

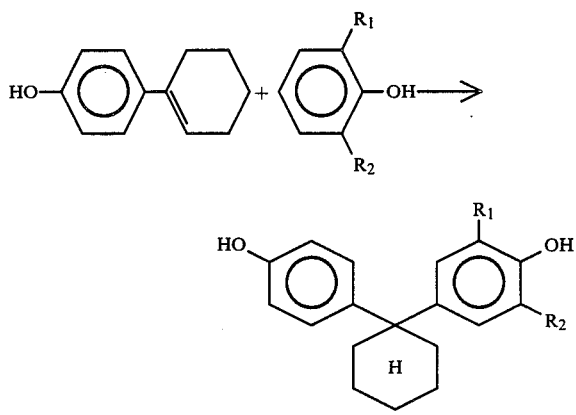

In this reaction equation, $R_1$ and $R_2$ are as defined above. Examples of the acidic catalyst used are metal halides, sulfuric acid, phosphoric acid, sulfonic acid and besides, activated clay or ion exchange resins as solid catalysts. The reaction temperature is in the range of 30° to 130° C., preferably 40° to 100° C. If the temperature is too high, the reaction may be accompanied with an isomerization reaction to reduce the yield of the objective compounds.

Since the objective compounds are all crystalline, their separation from the reaction mixture is carried out by filtration. Further, in order to improve filtrability, an organic solvent may be added during or after the reaction. The objective compounds may be further recrystallized to purify them to a sufficient purity for the object of the present invention.

The phenolic compounds of the present invention may be singly used as a color developer, respectively. Further it is also possible to use one or more kinds selected from the above compounds in combination with one or more kinds selected from other phenolic compounds. Examples of other phenolic compounds are other bisphenol compounds, p-hydroxybenzoic acid esters, p-hydroxyphthalic acid esters, hydroxyphenyl ketones.

The heat-sensitive recording material is a product obtained by coating upon a substrate, a heat-sensitive recording layer composed mainly of a dye and a color developer, and when the material is heated by thermal head, thermal stylus or the like, a color-developed phase is formed in the heat-sensitive recording layer to obtain a recorded image corresponding to the heating.

The dyes which form colors through the compounds of the present invention are electron donative i.e. basic dyes, which are intrinsically colorless, but when coupled with electron acceptive i.e. acidic substances such as phenolic compounds, have been considered to effect color development through electron donation and acceptance and particularly through the change of light absorption spectra at visible part. Concrete examples of the dyes are 3,3-bis(4-dimethylaminophenyl)-6-dimethylaminophthalide, 3,3-bis(4-dimethylaminophenyl)phthalide, 3-(4-dimethylaminophenyl)-3-(1,2-dimethylindol-3-yl)phthalide, 4,4'-bis-dimethylaminobenzhydryl benzyl ether, N-halophenyl-leucoauramines, benzoylleucomethylene blue, p-nitrobenzoylleucomethylene blue, 3-methyl-spiro-dinaphthopyran, 3-ethyl-spiro-dinaphthopyran, 3-propyl-spiro-dibenzopyran, 3-dimethylamino-7-methoxyfluroan, 3-diethylamino-6-methoxyfluoran, 3-diethylamino-7-methoxyfluoran, 3-diethylamino-7-chlorofluoran, 3-diethylamino-6-methyl-7-chlorofluoran, 3-diethylamino-6,7-dimethylfluoran, 3-(N-ethyl-p-toluidino)-7-methylfluoran, 3-diethylamino-7-N-acetyl-N-methylaminofluoran, 3-diethylamino-7-N-methylaminofluoran, 3-diethylamino-7-dibenzylaminofluoran, 3-diethylamino-7-N-methyl-N-benzylaminofluoran, 3-diethylamino-7-N-chloroethyl-N-methylaminofluoran, 3,7-bis(diethylamino)fluoran, 3-(N-ethyl-p-toluidino)-6-methyl-7-phenylaminofluoran, 3-(N-ethyl-p-toluidino)-6-methyl-7-(p-toluidino)fluoran, 3-diethylamino-6-methyl-7-phenylaminofluoran, 3-diethylamino-7-(2-carbomethoxyphenylamino)fluoran, 3-(N-ethyl-N-isoamylamino)-6-methyl-7-phenylaminofluoran, 3-(N-cyclohexyl-N-methylamino)-6-methyl-7-phenylaminofluoran, 3-pyrrolidino-6-methyl-7-phenylaminofluoran, 3-piperidino-6-methyl-7-phenylaminofluoran, 3-diethylamino-6-methyl-7-xylidinofluoran, 3-dimethylamino-7-(o-chlorophenylamino)fluoran, 3-diethylamino-7-(o-chlorophenylamino)fluoran, 3-pyrrolidino-6-methyl-7-(p-butylphenylamino)-fluoran, etc. The dyes, of course, are not limited to these exemplified dyes, and two kinds or more of the dyes may be used in combination.

In the heat-sensitive recording materials, the proportion of the dyes to the color developers used in the heat-sensitive recording layer should be choiced depending on the dyes and the color developers used and have no particular limitation, but generally, 1 to 50 parts by weight, preferably 2 to 10 parts by weight of the color developers per one part of the dyes may be used. The heat-sensitive recording layer is fixed onto a substrate by coating it with a coating composition containing the above dyes and the color developers as main constituents, followed by drying.

In the preparation of the coating composition, water is generally used as its medium, and the dyes and the color developers are usually together or separately ground and dispersed by means of a mix-grinding machine such as ball mill, attoritor, sand grinder, etc. Into such a coating composition, a binder is added in an amount of 10 to 70% by weight, preferably 15 to 50% by weight, based on the weight of the total solids. Examples of such a binder are starches, hydroxyethyl cellulose, methyl cellulose, carboxymethyl cellulose, gelatin, casein, acacia gum, polyvinyl alcohol, diisobutylene-maleic anhydride copolymer salts, styrene-maleic anhydride copolymer salts, styrene-acrylic acid copolymer salts, styrene-butadiene copolymer emulsion, etc. Further, various kinds of auxiliary agents may be added to the coating composition. Examples thereof are dispersants such as sodium dioctylsulfosuccinate, sodium dodecylbenzenesulfonate, sodium laurylsulfate, metal salts of fatty acids, etc., ultraviolet absorbers such as those of benzophenone group, benzotriazole group, etc., antifoamers, fluorescent dyes, coloring dyes, lubricants such as zinc stearate, calcium stearate, polyethylene wax, carnauba wax, paraffin wax, ester wax, etc., inorganic pigments such as kaolin, clay, talc, calcium carbonate, calcined clay, titanium oxide, diatomaceous earth, particulate silicic anhydride, activated clay, etc., sensitizers such as stearic amide, methylenebisstearic amide, oleic amide, palmitic amide, sperm oil oleic amide, coconut oil fatty acid amide, etc.

As the substrate, papers, plastic films, synthetic papers or the like may be used, but papers may be most preferably used in respect of cost and coating suitability.

As the method of forming the heat-sensitive recording layer, already known conventional techniques may be employed. For example, a coating composition is coated on a substrate by means of air knife coater, blade coater or the like, followed by drying, to form and fix a heat-sensitive recording layer. The layer usually has a dry weight in the range of 2 to 12 g, preferably 3 to 10 g per m². Further, in the case where the surface of the heat-sensitive recording layer is particularly required to be smooth, smoothing treatment may be carried out by means of supercalender, machine calender or the like.

The present invention will be described in more detail by way of Examples and Comparative examples. The part and % in these examples are by weight unless otherwise indicated.

EXAMPLE 1

Into a 500 ml capacity four-neck flask equipped with a stirrer, a thermometer, a reflux condenser and a feeding port were fed o-isopropylphenol (326 g) and p-cyclohexenylphenol (40 g), followed by heating the flask with stirring to raise the temperature of the contents to 60° C., and adding p-toluenesulfonic acid (1.5 g). When p-toluenesulfonic acid dissolved, exothermic reaction soon began. The contents were somewhat cooled and the temperature were kept at 60° C. After one hour, p-cyclohexenylphenol (40 g) was added through the feeding port. While the temperature was kept at 60° C., p-cyclohexenylphenol was further added in amounts of 30 g and 29 g at intervals of one hour. During this addition, a small amount of crystals of the objective compound was added as crystalline nucleic to deposit crystals of the objective compound. The operation was continued as it was. Sampling was sometimes carried out to follow the progress of the reaction by way of liquid chromatography. Four hours after the final addition of p-cyclohexenylphenol, p-cyclohexenylphenol was extinct whereby completion of the reaction was confirmed. The flask was then slowly cooled to make the temperature of the contents 15° C., followed by allowing them to stand overnight, filtering the contents in a slurry form by suction, sufficiently squeezing off the liquid, washing remaining crystals with a small amount of toluene, dissolving the crystals with toluene (500 ml) on heating, adding activated clay (1 g), filtering off the clay on heating, slowly cooling the filtrate to 10° C. to deposit white crystals, filtering off the crystals and drying them at 80° C. in vacuo, to obtain crystals (210 g) having a m.p. of 140° C., a hydroxyl value of 364 (theoretical value: 361.48) and a C/H ratio of 81.4:8.4 according to elementary analysis (theoretical value: 81.25:8.44). Thus it was confirmed that the crystals accorded with the objective 1-(4-hydroxyphenyl)-1-(3-isopropyl-4-hydroxyphenyl)-cyclohexane.

EXAMPLE 2

Example 1 was repeated except that o-propylphenol of Example 1 was replaced by o-cresol, 3,6-xylenol, o-ethylphenol, o-tertiary-butylphenol or o-cyclohexylphenol, to obtain the following compounds (m.p., hydroxyl value and C/H ratio according to elementary analysis being denoted in this order within parentheses):

2-1. 1-(4-hydroxyphenyl)-1-(3-methyl-4-hydroxyphenyl)-cyclohexane (179.5° C., 391, 81.1:7.7)
2-2. 1-(4-hydroxyphenyl)-1-(3,5-dimethyl-4-hydroxyphenyl)-cyclohexane (198° C., 374, 81.2:8.2)
2-3. 1-(4-hydroxyphenyl)-1-(3-ethyl-4-hydroxyphenyl)-cyclohexane (134° C., 381, 81.1:8.1)
2-4. 1-(4-hydroxyphenyl)-1-(3-tertiary-butyl-4-hydroxyphenyl)-cyclohexane (178° C., 344, 81.6:8.7)
2-5. 1-(4-hydroxyphenyl)-1-(3-cyclohexyl-4-hydroxyphenyl)-cyclohexane (167.5° C., 314, 81.9:8.9)

EXAMPLE 3

Preparation of liquid A:
A composition consisting of:
  3-(N-cyclohexyl-N-methylamino)-6-methyl-7-phenylaminofluoran: 10 parts,
  Methyl cellulose (5% aqueous solution): 5 parts, and
  Water: 40 parts,
was ground to an average particle diameter of 3 μm by means of a sand grinder.
Preparation of liquid B:
A composition consisting of:
  1-(4-hydroxyphenyl)-1-(3-isopropyl-4-hydroxyphenyl)cyclohexane: 20 parts,
  Methyl cellulose (5% aqueous solution): 5 parts, and
  Water: 55 parts, was ground to an average particle diameter of 3 μm by means of a sand grinder.

Formation of recording layer:

The liquid A (55 parts), the liquid B (80 parts), silica pigment (amount of oil absorbed: 180 ml/100 g) (15 parts), a 20% aqueous solution of oxidized starch (50 parts) and water (20 parts) were mixed together with stirring. The resulting coating composition was coated on a base paper of 50 g/m² so as to give a dry weight of 7 g/m², followed by drying to obtain a heat-sensitive recording paper.

EXAMPLES 4 AND 5

Example 3 was repeated except that in the preparation of the liquid B, 1-(4-hydroxyphenyl)-1-(3-isopropyl-4-hydroxyphenyl)cyclohexane was replaced by 1-(4-hydroxyphenyl)-1-(3-ethyl-4-hydroxyphenyl)cyclohexane (Example 4) or 1-(4-hydroxyphenyl)-1-(3-cyclohexyl-4-hydroxyphenyl)cyclohexane (Example 5), to obtain two kinds of heat-sensitive recording materials.

EXAMPLE 6

Preparation of liquid A:

A composition consisting of:
3-(N-cyclohexyl-N-methylamino)-6-methyl-7-phenylaminofluoran: 10 parts,
Methyl cellulose (5% aqueous solution): 5 parts, and
Water: 40 parts, was ground to an average particle diameter of 3 μm by means of a sand grinder.

Preparation of liquid B:

A composition consisting of:
1-(4-hydroxyphenyl)-1-(3-isopropyl-4-hydroxyphenyl)cyclohexane: 20 parts,
Methyl cellulose (5% aqueous solution): 5 parts, and
Water: 55 parts, was ground to an average particle diameter of 3 μm by means of a sand grinder.

Preparation of liquid C:

A composition consisting of:
2,2-di(4-hydroxyphenyl)propane: 20 parts,
Methyl cellulose (5% aqueous solution): 5 parts, and
Water: 55 parts, was ground to an average particle diameter of 3 μm by means of a sand grinder.

Formation of recording layer:

The liquid A (55 parts), the liquid B (80 parts), the liquid C (80 parts), silica pigment (amount of oil absorbed: 180 ml/100 g) (15 parts), a 20% aqueous solution of oxidized starch (50 parts) and water (10 parts) were mixed together with stirring. The resulting coating composition was coated on a base paper of 50 g/m² so as to give a dry weight of 7 g/m²; followed by drying to obtain a heat-sensitive recording material.

Comparative examples 1 and 2

Example 3 was repeated except that in the preparation of the liquid B of Example 3, 1-(4-hydroxyphenyl)-1-(3-isopropyl-4-hydroxyphenyl)cyclohexane was replaced by 2,2-di(4-hydroxyphenyl)propane (Comparative example 1) or 1,1-di(4-hydroxyphenyl)cyclohexanone (Comparative example 2), to obtain two kinds of heat-sensitive recording materials.

The six kinds of heat-sensitive recording materials obtained in Examples 3~6 and Comparative examples 1~2 were recorded using a high speed heat-sensitive facsimile recorder ("HIFAX 700" manufactured by Hitachi Seisakusho). The whiteness of the recording materials, the recording sensibility of the recorded images and the stability of the recorded images were as follows:

| | White-ness | Recording[*1] sensibility | Stability | |
|---|---|---|---|---|
| | | | Resistance to[*2] temperature and humidity | Resistance[*3] to plasticizer |
| Example 3 | o | 1.02 | o | o |
| Example 4 | o | 1.08 | o | o |
| Example 5 | o | 0.94 | o | Δ |
| Example 6 | Δ | 1.11 | o | o |
| Compar. ex. 1 | x | 0.88 | Δ | x |
| Compar. ex. 2 | o | 0.67 | Δ | o |

Evaluation standard:
o — No fogging is observed.
Δ — A certain fogging is observed.
x — A considerable fogging is observed.
Evaluation standard of stability:
o — Not extinct.
Δ — Somewhat extinct.
x — Considerably extinct.
[*1]The values of the recording sensibility are those obtained by measuring the recorded density just after recording by means of the above facsimile recorder, by means of Macbeth reflection density meter.
[*2]The resistance represents the state of the recorded sheet after it was preserved under the conditions of 40° C. and 90% RH for 24 hours.
[*3]The resistance represents the extinct state of the recorded image after the recorded sheet was placed on a polyvinyl chloride film and 24 hours lapsed.

What is claimed is:

1. Novel phenolic compounds expressed by the general formula I

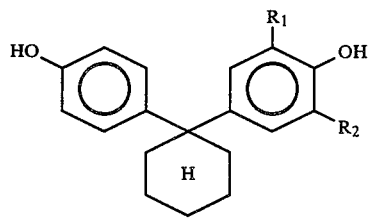

wherein $R_1$ represents an alkyl group or a cycloalkyl group and $R_2$ represents hydrogen atom or an alkyl group.

2. A process for producing phenolic compounds expressed by the general formula I

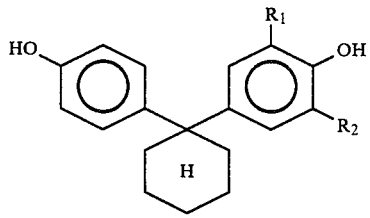

wherein $R_1$ represents an alkyl group or a cycloalkyl group and $R_2$ represents hydrogen atom or an alkyl group, which process comprises reacting p-cyclohexenylphenol with an o-substituted phenol expressed by the general formula
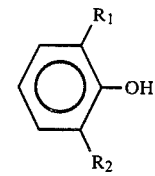
wherein $R_1$ and $R_2$ are as defined above, in the presence of an acidic catalyst selected from the group consisting of metal halides, sulfuric acid, phosphoric acid, sulfonic acid, activated clay and ion exchange resins, at temperatures of from 30° to 130° C.
* * * * *